United States Patent [19]
Evans et al.

[11] Patent Number: 5,891,627
[45] Date of Patent: Apr. 6, 1999

[54] POLYMORPHIC LOCUS

[75] Inventors: Glen A. Evans, Encinitas; Licia Selleri, Del Mar; James H. Eubanks, San Diego, all of Calif.

[73] Assignee: The Salk Institute for Biological Studies, La Jolla, Calif.

[21] Appl. No.: 420,629

[22] Filed: Apr. 12, 1995

Related U.S. Application Data

[63] Continuation of Ser. No. 773,099, Oct. 9, 1991, abandoned.

[51] Int. Cl.$^6$ .............................. C12Q 1/68; C12P 19/34
[52] U.S. Cl. .............................................. 435/6; 435/91.2
[58] Field of Search .................................. 435/6, 5, 91.1, 435/91.2; 935/77, 78

[56] References Cited

U.S. PATENT DOCUMENTS

| | | | |
|---|---|---|---|
| 4,741,998 | 5/1988 | Herr et al. .................................. | 435/6 |
| 4,835,098 | 5/1989 | Orr et al. ..................................... | 435/6 |
| 4,971,902 | 11/1990 | Nepom ........................................ | 435/6 |
| 5,024,934 | 6/1991 | Lee .............................................. | 435/6 |
| 5,075,217 | 12/1991 | Weber ......................................... | 435/6 |
| 5,198,345 | 3/1993 | Gwynne et al. ........................ | 455/69.1 |

FOREIGN PATENT DOCUMENTS 0418960  3/1991  European Pat. Off. .

OTHER PUBLICATIONS

Eubanks et al., Genomics 11:720–729 (1991) "Isolation, localization, and physical mapping . . ."
Botstein et al., Am. J. Hum. Genet. 32:314–331 (1980) "Construction of a genetic linkage map . . ."
Chamberlain et al., Nucl. Acid. Res 14:3409–3424 (1986) "The structure of HSAG–1, a middle . . ."
P.N.A.S. 86:212–216 (Jan. 1989) Boerwinkle, E; et al "Rapid typing of tandemly repeated . . . ".
J. Biol. Chem 266:9610–9616 (1991) Kunze, N; et al "Structure of human type I DNA topoisomerase".
Gill, et al., Forensic application of DNA 'fingerprints', Nature, vol. 318, pp. 577–579, Dec. 1985.
Jeffreys, et al., Individual–specific 'fingerprints' of human DNA, Nature, vol. 316, pp. 76–79, Jul. 1985.
Gill, et al., An evaluation of DNA fingerprinting for forensic purposes, Electrophoresis 1987, 8, 38–44.
Semenza et al, J. Biol. Chem 259:6045–6048 (1984).

*Primary Examiner*—Eggerton A. Campbell
*Attorney, Agent, or Firm*—Fish & Richardson P.C.

[57] ABSTRACT

Nucleotide sequence defining a polymorphic locus useful for identification of an individual. Also disclosed are oligonucleotide primers useful in amplification of the locus and methods for detecting the amplified locus.

16 Claims, 9 Drawing Sheets

```
ATATACAAGGCCTTGCTGCTGCCCGGCCTGATGGAGAGGCCGGCTGCCACCTTGAGCCAGAGCAGGTAGGTGTGCTGCTCGTGCAGACCCCGAATGCC
TTGAGTGGGGTCCGGGGCAGGGTGCACGCGGGTCAGGTAGTGCTCCGAGTGCTCAGTCCGAGTGCCTTGAGTGGGGTCCGGGGCAGGGTGCACA
CACTCAGTAGGTGCTGGTAGTGCAGACCCCGAATACCTTGAGTGGGGTCCGGGGCAGGGTTGCACATACTCAGGCCCATCTCCACCATGGGCACAT
GGCCTCTTTTTGACAAAGTATCTCTGCCTAGTCCCCTGGGTGTGGTCAATCATTTATCCTTCTCTTGTATGTGTATGTATATGTATATGTATATGT
ATATGTATATGTATATGTATATGTACGTGTACGTGTACGTGTATGTATATGTATATGTATATGTATATGTATATGTATATGTATATGT
ATATGTATATGTATATGTATATGTATATGTATATGTATATGTATATGTATATGTATATGTATATGTATATGTATATGTATATGTATATGT
ATATGTATATGTATATGTATATGTATATGTATATGTATATGTATATGTATATGTATATGTATATGTATATGTATATGTATATGTATATGT
ATATGTATATGTATATGTATATGTATATGTATATGTATATGTATATGTATATGTATATGTATATGTATATGTATATGTATATGTATATGT
GTGTATGTATCGGGTACCGTAGTCCCCCTTATCCACTGGGACATGTTCCAGACCCCCAGCGGATGCTG
```

FIG. 2A

POLYMORPHIC LOCUS

This is a continuation of application Ser. No. 07/773,099 filed on Oct. 9, 1991, now abandoned.

BACKGROUND OF THE INVENTION

1. Field of the Invention

This invention generally relates to the detection of a polymorphic locus nucleotide sequence which can be used to identify an individual of a species.

2. Related Art

Mammalian genomes consist of unique DNA sequences interspersed with moderately and highly repetitive DNA sequences. Gene mapping by meiotic linkage analysis has traditionally been carried out using variations in unique sequence DNA, such as restriction fragment length polymorphisms (Botstein, et al., *Am J. Hum. Genet,* 32:314–331, 1980), as genetic markers. Recently, variations in the repetitive sequence elements such as minisatellite or variable number tandem repeat (VNTR) sequences (Jeffreys, et al., *Nature,* 314:67–73, 1985; Nakamura, et al., *Science,* 235:1616–1622, 1987), and microsatellite or variable simple sequence motifs (VSSM) (Litt and Luty, *Am. J. Hum. Genet.,* 44:397–401, 1989; Weber and May, *Am. J. Hum. Genet.,* 44:388–396, 1989) have been found to be useful for linkage studies. One advantage to the use of repetitive sequence variations rather than unique sequence variations is the apparent greater number of alleles present in normal populations when compared to restriction fragment length polymorphisms (RFLPs). A second advantage is the ability to readily detect sequence length variations using the polymerase chain reaction to facilitate the rapid and inexpensive analysis of large numbers of DNA samples.

Microsatellite elements consist of simple mon-, di-, or tri-nucleotide sequences where alleles differ by one or more repeat units (Luty, et al, *Am.J. Hum. Genet.,* 46:776–783, 1990; Tautz, et al., *Nature,* 322:652–656, 1986; Weber and May, *Am. J. Hum. Genet.,* 44:388–396, 1989). Minisatellites, or VNTR sequences, typically have a repeat unit of 20 to several hundred nucleotides and alleles differ by as little as one repeat unit. Among simple sequences, the $(TG)_n$ or $(CA)_n$ repeat elements have recently proven extremely useful for meiotic mapping since (1) they are abundant in the genome, (2) display a large number of different alleles, and (3) can be rapidly assayed using the polymerase chain reaction (Litt and Luty, *Am. J. Hum. Genet.,* 44:397–401, 1989; Weber and May, *Am. J. Hum. Genet,* 44:388–396, 1989).

A number of other short sequence motifs have been found in mammalian (Hellman, et al., *Gene,* 68:93–100, 1988; Knott, et al., *Nuc. Acids Res.,* 14:9215–9216, 1986; Litt and Luty, *Am. J. Hum. Genet,* 44:397–401, 1989; Milstein, et al., *Nuc. Acids Res.,* 12:6523–6535, 1984; Stoker, et al., *Nuc. Acids Res.,* 13:4613–4621, 1985; Vassart, et al., *Science,* 233:683–684, 1987; and Vergnaud, *Nuc. Acids Res.,* 17:7623–7630,1989), and avian (Gyllensten, et al., *Nuc. Acids Res.,* 17:2203–2214, 1989; Longmire, et al., *Genomics,* 2:14–24, 1988) genomes and are thought to accumulate by DNA slippage during replication (Tautz, et al., *Nature,* 322:652–656, 1986) or unequal recombination events (Wolff, et al., *Genomics,* 5:382–384, 1989). Many of these repeat elements display a high degree of genetic variation and thus are also useful for meiotic mapping.

The VNTR sequence isolated by Jeffreys contains an invariant core sequence GGGCAGGAXG (SEQ ID NO:1) which bears some similarities to the chi sequence of phage lambda (Wolff, et al., *Genomics,* 5:382–384, 1989) and is detected by a restriction fragment of bacteriophage M13 (Vassart, et al., *Science,* 233:683–684, 1987). Similar repeat elements have been detected by Nakamura, et al. (*Science,* 235:1616–1622, 1987) and contain a similar, but distinctive, common core unit GGG—GTGGGG (SEQ ID NO:2). Elements of this type occur within several known gene sequences including the β globin locus. Similar VNTR elements have been described within the apolipoprotein B (Boerwinkle, et al., *Proc. Natl. Acad. Sci. USA,* 86:212–216, 1989; Knott, et al., *Nuc. Acids Res.,* 14:9215–9216, 1986) and collagen type II genes (Stoker, et al., *Nuc. Acids Res.,* 13:4613–4621, 1985) and contain a distinct AT-rich motif. Though a physiological function for repetitive elements of this type has not been defined, they have been suggested as potential hot spots for chromosome recombination (DeBustros, et al., *Proc. Natl. Acad. Sci.,* 85:5693–5697, 1988) or elements important for the control of gene expression (Hellman, et al., *Gene,* 68:93–100, 1988; Milstein, et al., *Nuc. Acids Res.,* 12:6523–6535, 1984).

In addition to linkage analysis, highly variable probes are useful for identity testing in practical applications such as paternity testing and forensics. One disadvantage to the use of VNTR probes, is the necessity for carrying out Southern blot analysis for allele detection. Frequently DNA samples for these applications are of poor quality and low quantity. The analysis of $(CA)_n$ polymorphisms may be difficult since the elements may be short and alleles may differ by as little as 2 nucleotides, necessitating the use of DNA sequencing gels and radioactive labeling for allele detection (Litt and Luty, *Am. J. Hum. Genet.,* 44:397–401, 1989; Weber and May, *Am. J. Hum. Genet.,* 44:388–396, 1989). Consequently, an unfulfilled need exists for a technique which can detect a unique DNA sequence in specimens of poor quality or in low quantity without having to rely on isotopic detection. The present invention provides such a technique.

SUMMARY OF THE INVENTION

The present invention arose from the discovery of a novel DNA sequence which defines a polymorphic locus which can be used to identify an individual of a species. The positive strand of this polymorphic locus comprises a hexanucleotide sequence:

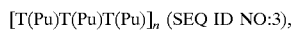

$[T(Pu)T(Pu)T(Pu)]_n$ (SEQ ID NO:3), wherein T is thymine, Pu is independently a purine and n is 1 to about 1000.

In the process of discovering the polymorphic locus, oligonucleotide(s) which can be used as pimers were identified. These oligonucleotides align with the unique flanking regions of the locus thereby allowing amplification of the locus by such techniques as polymerase chain reaction (PCR). These oligonucleotides represent a highly conserved sequence which has been found in all individuals examined thus far.

The present invention represents a major improvement over other techniques used to detect or "fingerprint" DNA from specimens. A major advantage afforded by the invention is that the use of radioactive labels is unnecessary. For example, although each individual has only one genomic polymorphic locus, the "universal" oligonucleotide(s) primers allow amplification of the locus such that the use of radioactive labels is unnecessary. Further, because only the polymorphic locus is amplified and typically rather large, analysis can be performed using a simple agarose gel rather

DETAILED DESCRIPTION OF THE PREFERRED EMBODIMENT

Figure 1:
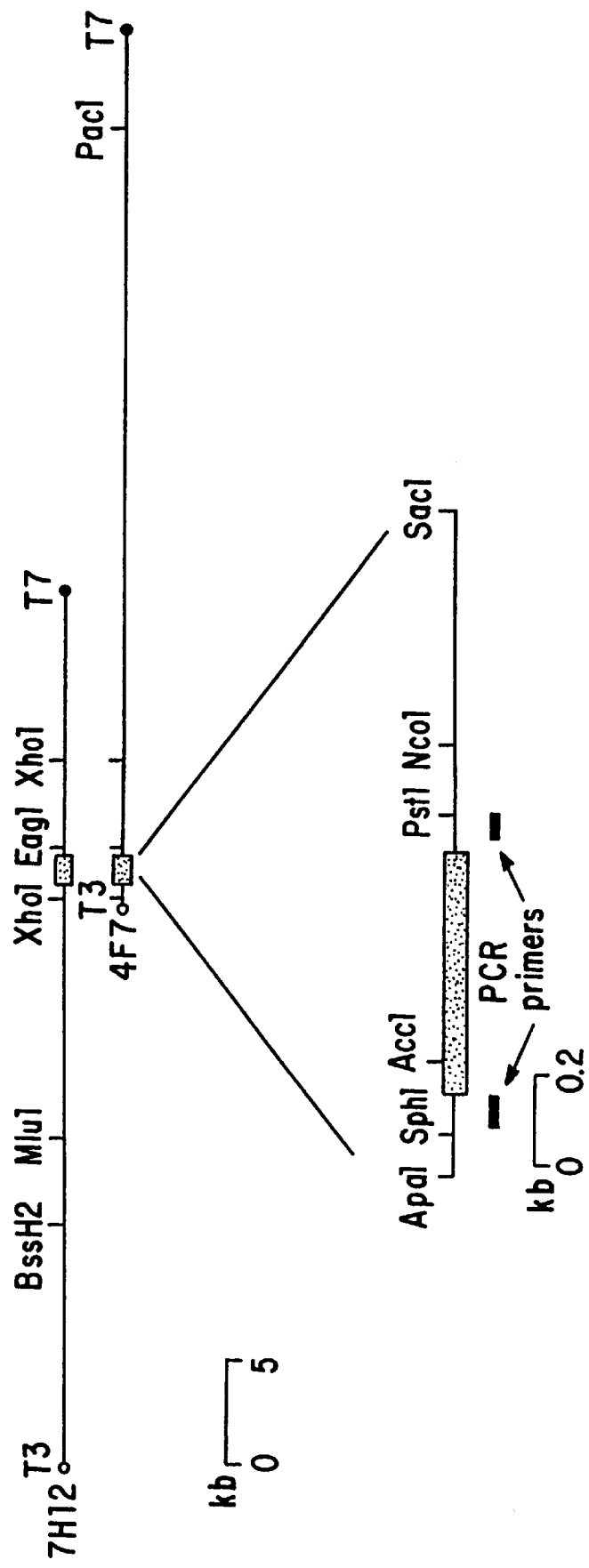
FIG. 1 Physical map of the cosmids 4F7 and 7H12 showing the position of rare restriction sequences and the location of the polymorphic repetitive element. Restriction maps were determined using combined digestion with multiple restriction enzymes as well as oligo-end labeling (Evans, et al., *Proc. Natl. Acad. Sci. USA*, 86:5030–5034, 1989). An ApaI-SacI fragment of cosmid 4F7 was purified by preparative agarose gel electrophoresis and subcloned into the plasmid vector Bluescript for DNA sequencing. The location of the polymorphic repetitive sequence is indicated by the shading area. The positions of the oligonucleotide sequences used for PCR detection are indicated by dark bars. These were constructed in vector sCos-1 (Evans, et al., *Proc. Natl. Acad. Sci. USA*, 86:5030–5034,1989), which has T3 and T7 bacteriophage promoters flanking the human DNA insert and the orientation of the insert within the vector is indicated.

The present invention relates to a previously unknown nucleotide sequence which defines a unique genomic polymorphic locus found as a single copy in the genome. This polymorphic locus is highly useful for identifying an individual of a species using a nucleic acid containing specimen. As such, the invention provides a novel method for identifying an individual based, for example, on forensic analysis.

In general, the positive strand of the polymorphic locus can be characterized as comprising a hexanucleotide sequence: $[T(Pu)T(Pu)T(Pu)]_n$ (SEQ ID NO:3), wherein T is thymine, Pu is independently a purine, and n is 1 to about 1000. As further described herein, studies have shown that individuals differ as to the nature of the purines in the hexanucleotide and also as to the number of hexanucleotides present in the polymorphic locus. Thus, a given individual can be characterized based upon the size of that individual's polymorphic locus. In the present invention, the hexanucleotide polymorphic locus sequence is amplified to facilitate detection using oligonucleotide primers described below. Following amplification, the polymorphic locus is analyzed with respect to its molecular weight, for example, by gel separation. Although the amplified polymorphic locus may be detected using various labels and techniques known to those of skill in the art, the present invention lends itself to the use of non-isotopic detection, for example, by staining with ethidium bromide.

The hexanucleotide sequence comprising the genomic polymorphic locus may also include a restriction site for an endonuclease, such as the AccI restriction endonuclease site. The presence of such restriction site further enhances the analysis of the polymorphic locus by allowing additional characterization of the polymorphic locus. Thus, while two individuals may appear to have a polymorphic locus which has the same molecular weight in the absence of treatment with the appropriate restriction enzyme, it is possible to differentiate between these two individuals when one individual's amplified polymorphic locus contains the susceptible restriction site.

The detection of the polymorphic locus is accomplished by oligonucleotide(s) which are primers for amplification of the genomic polymorphic locus. These unique oligonucleotide primers were produced based upon identification of the flanking regions contiguous with the polymorphic locus. These oligonucleotide primers comprise sequences which are capable of hybridizing with the flanking nucleotide sequence GCCTAGTCCCTGGGTGTGGTC (SEQ ID NO:4) and/or GGGGACATGTTCCCAGACCCCC (SEQ ID NO:5) and sequences complementary thereto.

The primers of the invention embrace oligonucleotides of sufficient length and appropriate sequence so as to provide specific initiation of polymerization on a significant number of nucleic acids in the polymorphic locus. Specifically, the term "primer" as used herein refers to a sequence comprising two or more deoxyribonucleotides or ribonucleotides, preferably more than three, which sequence is capable of initiating synthesis of a primer extension product, which is substantially complementary to a polymorphic locus strand. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 15–22 or more nucleotides, although it may contain fewer nucleotides.

Primers of the invention are designed to be "substantially" complementary to each strand of polymorphic locus to be amplified. This means that the primers must be sufficiently complementary to hybridize with their respective strands under conditions which allow the agent for polymerization to perform. In other words, the primers should have sufficient complementarity with the flanking sequences to hybridize therewith and permit amplification of the polymorphic locus. Preferably, the primers have exact complementarity with the flanking sequence strand.

Oligonucleotide primers of the invention are employed in the amplification process which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA Polymerase I (Klenow) and nucleotides, results in newly synthesized + and −strands containing the target polymorphic locus sequence. Because these newly synthesized sequences are also templates, repeated cycles of denaturing, primer annealing, and extension results in exponential production of the region (i.e., the target polymorphic locus sequence) defined by the primer. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters*, 22:1859–1862, 1981). One method for synthesizing oligonucleotides on a modified solid support is described in U.S. Pat. No. 4,458,066.

Any nucleic acid specimen, in purified or nonpurified form, can be utilized as the starting nucleic acid or acids, provided it contains, or is suspected of containing, the specific nucleic acid sequence containing the polymorphic locus. Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA or RNA utilized herein may be extracted from a body sample, such as blood, tissue material such as chorionic villi, or amniotic cells by a variety of techniques such as that described by Maniatis, et al. (*Molecular Cloning*, 280:281, 1982). If the extracted sample is impure (such as plasma, serum, or blood), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily.

Where the target nucleic acid sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (*CSH-Quantitative Biology*, 43:63, 1978) and techniques for using RecA are reviewed in C. Radding (*Ann. Rev. Genetics*, 16:405–437,1982).

If the nucleic acid containing the sequence to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be partially complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess (for genomic nucleic acid, usually about $10^8:1$ primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, E. coli DNA polymerase I, Klenow fragment of E. coli DNA polymerase 1, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

The newly synthesized polymorphic locus strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleotides, and primers may be added, if necessary, for the reaction to proceed under the conditions prescribed above. Again, the synthesis will b e initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the target polymorphic locus nucleic add sequence to the extent necessary for detection. The amount of the specific nucleic acid sequence produced will accumulate in an exponential fashion.

The amplified product may be detected by analyzing it by Southern blots without using radioactive probes. In such a process, for example, a small sample of DNA (e.g., from peripheral blood lymphocytes) containing a very low level of the nucleic acid sequence of the polymorphic locus is amplified, and analyzed via a Southern blotting technique. The use of non-radioactive probes or labels is facilitated by the high level of the amplified signal.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

MATERIALS AND METHODS

Cosmids and Libraries

Genomic cosmid clones were isolated from a chromosome 11 q-specific cosmid library constructed in vector sCos-1 (Evans, et al., *Gene*, 79:9–20, 1989) and arrayed on nitrocellulose filters (Evans, et al., *Proc. Natl. Acad. Sci. USA*, 86:5030–5034, 1989). This library is representative of 11q12-11qter and has been used in the construction of cosmid contigs (Evans and Lewis, *Proc. Natl. Acad. Sci. USA*, 86:5030–5034, 1989) as well as for the isolation of landmark mapping clones (Lichter, et al., *Science*, 247:64–69, 1990). Cosmid clones were amplified and DNA was prepared as described by Evans and Wahl (*Methods. Enzymol.*, 152:604–610, 1987).

Oligonucleotide Probes

Oligonucleotides were synthesized using a PCR-MATE Oligonucleotide Synthesizer (Applied BioSystems, Inc.). A 60-base oligonucleotide corresponding to a portion of the DNA sequence of the rat D2 dopamine receptor cDNA (Bunzow, et al., *Nature*, 336:783–787, 1988) (CCACTCACCCACCACCTCCAGGTAGACAACCCAC-GGCATTACCAGTGT GGCCACCAGMG) (SEQ ID NO:6) was used for initial isolation of cosmid containing G-protein receptor-like motifs. Additional oligonucleotides for PCR analysis were synthesized corresponding to unique sequences flanking the repetitive element, shown in FIG. 2A. Oligonucleotides used for YAC screening by PCR are also shown in FIG. 2A.

Isolation of Clones

Arrayed cosmid colonies were distributed on nitrocellulose or nylon filters, fixed using the Grunstein procedure (Evans and Lewis, Proc. Natl. Acad. Sci. USA, 86:5030–5034, 1989; Evans and Wahl, Methods. Enzymol., 152:604–610, 1987) and prehybridized at 60° C. overnight. The oligonucleotide probe was radiolabeled using polynucleotide kinase and gamma $^{32}$P-nucleotide and hybridized to the filters at 42° C. for 12 hours. Washing was carried out in 0.4×SSC at 55° C. and the filters were then exposed to Kodak XAR film overnight at –70° C.

PCR Reactions

Genomic DNA was prepared from 20 ml of fresh whole blood obtained by venipuncture or from one of 3 cell lines known to be karyotypically normal for this region of chromosome 11. Specific amplification of the repetitive locus was performed using the polymerase chain reaction primed with oligonucleotides specific for unique sequences flanking the repetitive sequence element. The amplification products were then electrophoresed on 2% agarose gels and DNA visualized by staining with ethidium bromide. The amplification procedure involved heat denaturation 45 sec at 92° C., annealing for 1 min at 66° C., and extension at 72° C. for 30 seconds cycling for 35 rounds. The reaction conditions used a final concentration of 0.5 $\mu$M each of oligonucleotide primers, 1 mM dNTP's, 1×Taq I Buffer, and 1 unit Taq Polymerase (Stratagene, San Diego, Calif.) in 30 $\mu$l reactions. Amplification was carried out using a Bellco DNA Pacer thermal cycler.

Southern Blot Hybridization

10 $\mu$g of human genomic DNA obtained from HeLa cells was digested with 25 units of restriction enzyme for 12 hours, and separated for 15 hours at 30 volts on a 0.8% agarose gel. The DNA was transferred to nitrocellulose filters using the standard Southern procedure, and hybridized with a 500 base pair Acc 1-Pst 1 fragment, containing primarily the repetitive elements. Hybridization was carried out using a final concentration of 2.6×Denhardt's reagent, 43% formamide, 4.25×SSC, 1.0 mg/ml salmon sperm DNA, and 10% dextran sulfate, at 42°C., for 12–18 hours (Evans and Wahl, Methods. Enzymol., 152:604–610, 1987).

DNA Sequence Analysis

DNA sequences were determined using double-stranded di-deoxy sequencing reactions labeled with $^{35}$S dCTP. Restriction fragments from the cosmid clone were purified and subcloned into the Bluescript (Stratagene) plasmid vector. DNA sequencing was carried out using the modified T7 DNA polymerase (US Biochem) and primers specific for the T7 or T3 promoter sequences in the Bluescript vector. Electrophoresis was carried out on 6% acrylamide gels containing urea on a standard sequencing apparatus (CBS Scientific). DNA sequences were read and analyzed using programs from the University of Wisconsin Genetics Computer Group version 6.0 package (Devereaux, et al, Nuc. Acids Res., 12:387–395, 1984) running on a VAX 8600 computer.

In situ Hybridization

Fluorescent in situ suppression hybridization was carried out as previously described (Lichter, et al., Science, 247:64–69, 1990; Selleri, et al., Proc. Natl. Acad. Sci. USA, 88:887–891, 1990). Metaphase chromosomes were prepared from a human B lymphoblast cell previously shown to have a normal human karyotype. Cosmid DNA was prepared using a "miniprep" procedure (Evans and Wahl, Methods. Enzymol., 152:604–610, 1987), or, alternatively, by cesium chloride "banding", treated with RNase, and labeled with biotinylated dCTP and dUTP (Selleri, et al., Proc. Natl. Acad. Sci. USA, 88:887–891, 1990; Selleri, et al., Genetic Analysis Techniques and Applications, 8:59–66, 1991). Hybridization reactions were carried out using standard conditions (Lichter, et al., Science, 247:64–69, 1990) and images were obtained using a BioRad MRC 500 confocal microscope equipped with an Ar gas laser. Position measurements were performed as described by Lichter, et al., (Science, 247:64–69, 1990) by determining the distance from the 11p telomeres (FLpter) on at least 30 chromosomes 11. More than 95% of labeled chromosomes showed distinct hybridization signals on both sister chromatids.

Pulsed Field Gel Electrophoresis

Agarose plugs containing high molecular weight DNA were prepared from human B lymphoblastoid cell lines WI-L2–729 and HHW1069 (Heitzman, et al., Mol. Biol. Med., 1:235–243, 1983) equilibrated with Universal digestion buffer (Stratagene), and digested overnight with 15–50 units of restriction endonuclease. The digested plugs were then loaded on a 1% agarose gel, and electrophoresed 22–25 hours at 16° C. using the HEX-CHEF (Chu, et al., Science, 234:1582–1585, 1986) electrode configuration.

Yeast Artificial Chromosomes

Yeast artificial chromosomes (YAC's) containing the 4F7 polymorphic locus were isolated from a human genomic YAC library constructed in pYAC-4 (Burke, et al., Science, 236:806–812, 1987) made available by M. Olson (Washington University, St. Louis). Screening was carried out using a modified pool strategy (Brownstein, et al., Science, 244:1348–1351, 1989; Green and Olson, Proc. Natl. Acad. Sci. USA, 87:1213–1217,1990) using the polymerase chain reaction. The isolated YAC clones were characterized by pulsed field gel analysis, restriction mapping and hybridization to cosmid clones.

The following examples are intended to illustrate but not limit the invention. While they are typical of those that might be used, other procedures known to those skilled in the art may alternatively be used.

EXAMPLE 1

Characterization of Polymorphic Locus Hexameric Motif

In the course of using a 60 nucleotide sequence corresponding to the predicted second transmembrane domain of a rat D2 dopamine receptor cDNA (Bunzow, et al., Nature, 336:783–787, 1988; Monsma, et al., Nature, 342:926–929, 1989), several cosmid clones were identified in arrayed chromosome-specific cosmid libraries (Evans, G. A., BioEssays, 13:39–44, 1991; Evans and Lewis, Proc. Natl. Acad. Sci. USA, 86:5030–5034, 1989) with potential structural relationships to the G-protein coupled receptor gene family as well as several loci on chromosome 11 containing cross-hybridizing sequences. Two cosmids, designated 4F7 and 7H12 (FIG. 1), showed a strong hybridization signal to this oligonucleotide and contain a sequence cross-hybridizing with the D2 dopamine receptor transmembrane domain. In addition to this sequence, a highly repetitive element was detected in the region of overlap of the two cosmids and further characterized (FIG. 1).

Figure 2B:
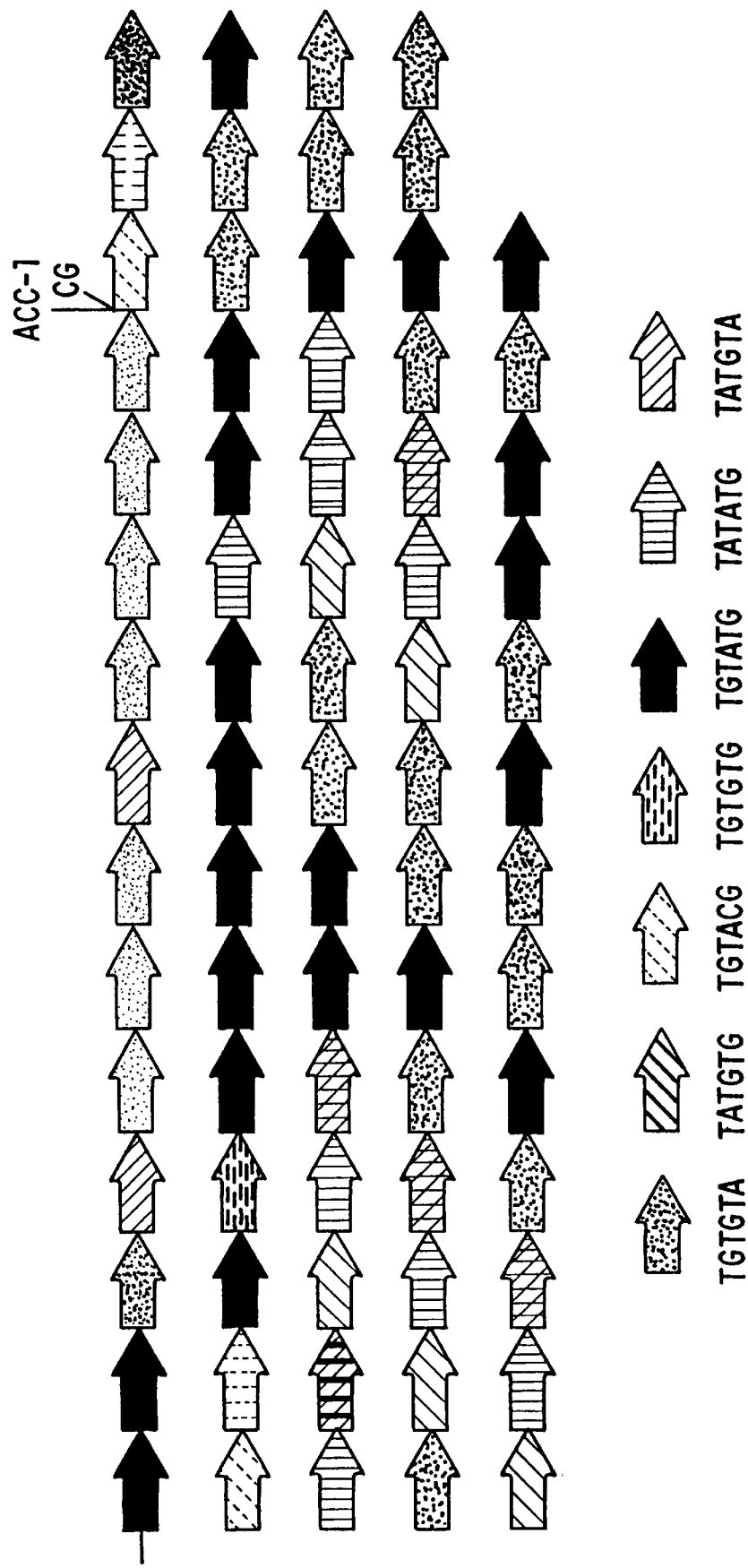
FIG. 2 A. DNA sequence analysis of a portion of the 4F7 repetitive element. The location of the repetitive element, extending over 412 base pairs in this individual, is shown underlined. The unique flanking sequences which serve as priming sites for PCR amplification for allele detection are double-underlined, as is the AccI restriction site located within the repeat unit. The location of PCR primers for YAC screening are shown with dotted-underlines. One of the two priming sequences overlaps with one used for allele detection. B. Structure of the polymorphic element is shown diagrammatically as repetitive hexanucleotide sequences of the form $[T(Pu)T(Pu)T(Pu)]_n$ (SEQ ID NO:3).

Because this repeat element was potentially useful as a genetic marker, further characterization was carried out. A 1.9 kb Apa 1-Sac 1 restriction fragment containing this repetitive sequence was subcloned into Bluescript (Strategene, San Diego, Calif.) and the DNA sequence of the repetitive element was determined (FIG. 2A). The DNA sequence revealed a highly degenerate repetitive hexamer motif spanning 438 base pairs consisting of 73 repeats of the form [T(Pu)T(Pu)T(Pu)]$_n$ (SEQ ID NO:3), and a single dinucleotide insertion contributing the Acc1 site. The most common motif found in this element was TATATG (41%). Along with TGTATG (29%) and TATGTG (12%), these three motifs comprised the majority of the repeat element which was flanked by unique sequences. Superimposed on this hexameric repeat, was a more complex, high order repeat where the repeat units of TATATG (Type A), TGTATG (Type B), or TATGTG (Type C) was repeated in a pattern AAABAC or AAABAB (FIG. 2B). This higher order repeat unit is most easily observed at the 3' end of the element.

EXAMPLE 2

Detection of Polymoprhic Locus in Various Individuals

Figure 3:
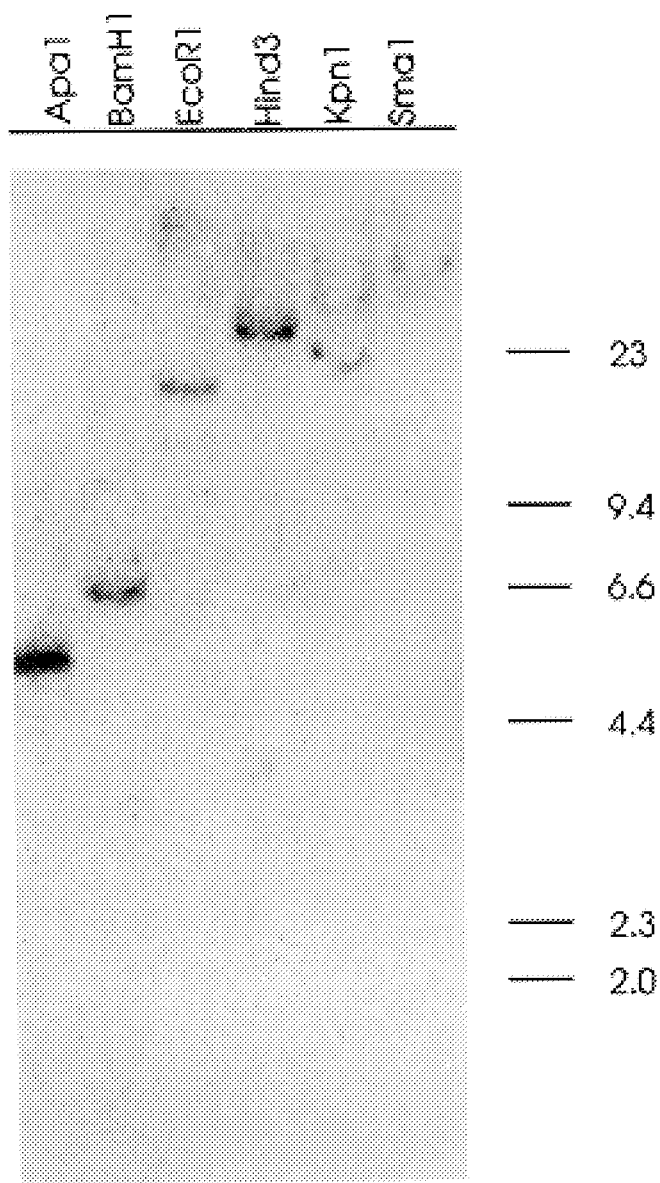
FIG. 3 A unique probe derived from the 4F7 cosmid and containing the repetitive element was used to detect genomic fragments by Southern blot analysis of human genomic DNA. DNA was digested with the indicated restriction enzymes and hybridization carried out as described in Methods. Band sizes were determined to be: Apa 1, 5.7 kb; BamH I, 6.6 kb; Eco R1, 18 kb; Hind III, 26 kb; Kpn I, 22 kb; and Sma I>25 kb. Size markers are HindIII fragments of bacteriophage lambda.

To determine if this element was highly repetitive in the human genome, or represented multiple sites, the Apa1-Sac1 restriction fragment was used as a probe for Southern blot analysis on human DNA from a number of sources. In spite of this complex repetitive element, a unique single-band hybridization signal was obtained under moderate stringencies, indicating a single copy representation in the human genome (FIG. 3). While unique in any one individual, comparison of the restriction pattern on Southern blots using DNA samples from different individuals suggested that this element might be polymorphic and thus be useful as a mapping probe.

Figure 4:
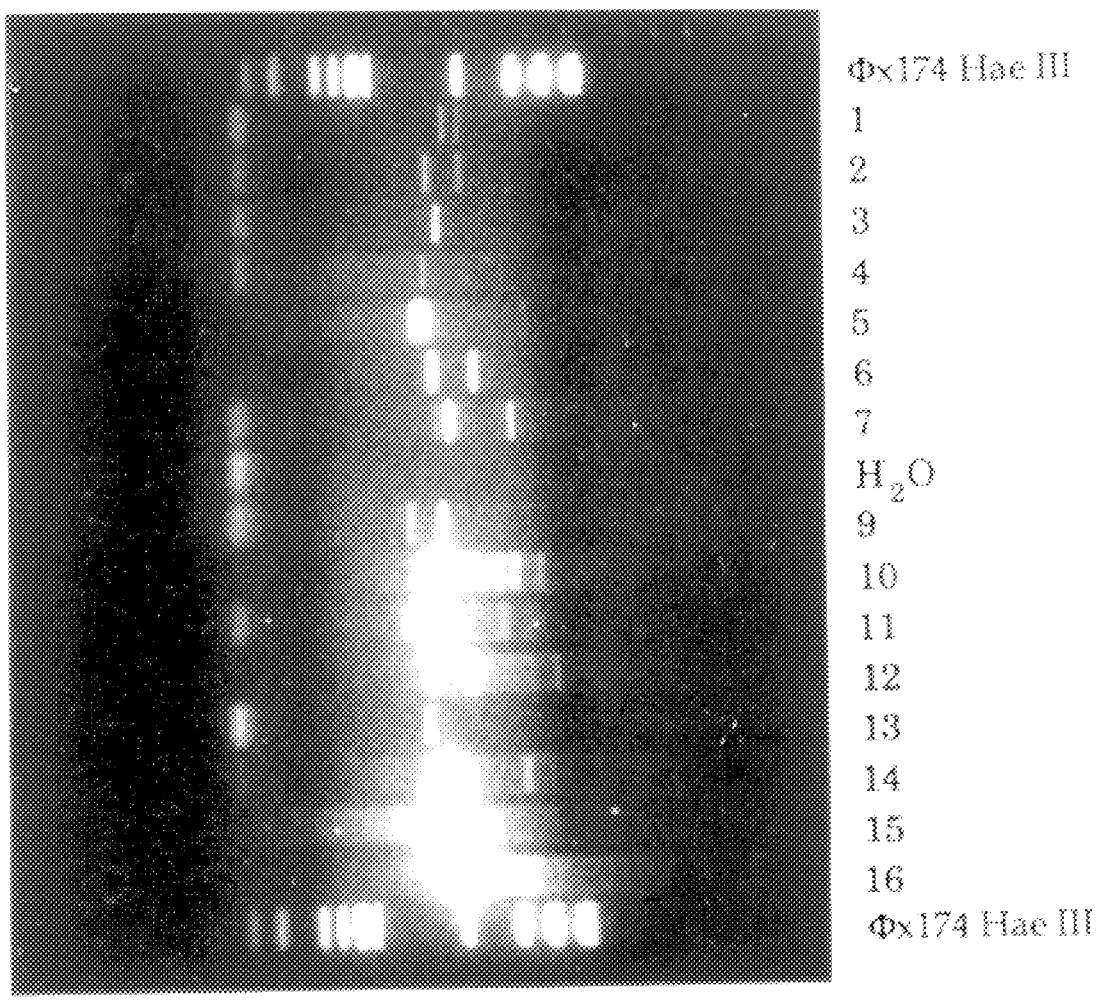
FIG. 4 Analysis of multiple individuals for the 4F7 repetitive element by PCR demonstrates a large number of alleles. Lanes 1–7, and 9–15 represent amplification products of DNA prepared from different individuals. A 20 ml blood sample was used to prepare genomic DNA which was analyzed using the PCR primer set shown in FIG. 3A. Amplification products were analyzed on a 2% agarose gel and amplified products visualized by staining with ethidium bromide. Lane 8 is a blank control, and lane 26 is the product amplified from cosmid 4F7. This analysis demonstrates the presence of at least 10 different alleles in 15 individuals.

To analyze the presence and degree of polymorphism, and to provide for rapid and efficient analysis of DNA genotype on multiple samples, an assay system was devised for this unique repeat element based on amplification using the polymerase chain reaction (Saiki, et al., Science, 230:1350–1354, 1985). Synthetic oligonucleotides were prepared complementary to the unique sequence flanking the 4F7 repetitive element (FIG. 2A). PCR amplification using these primers was found to result in unique DNA fragment lengths which could be easily detected on simple agarose gels. To evaluate the polymorphism of this repeat element, DNA was obtained from 15 unrelated individuals and subjected to PCR amplification (FIG. 4). In each case, two amplification products, presumably representing two alleles of the 4F7 repeat element, were detected and could be easily distinguished on agarose gels. Among the 15 individuals tested, at least 10 alleles were detected ranging in size from 300 to 900 bp. No allele was detected less than 300 bp and one individual appeared to be homozygous or to have two alleles which could not be distinguished in size. This analysis suggests that the length of this sequence is highly polymorphic and that both alleles can be detected.

Figure 5:
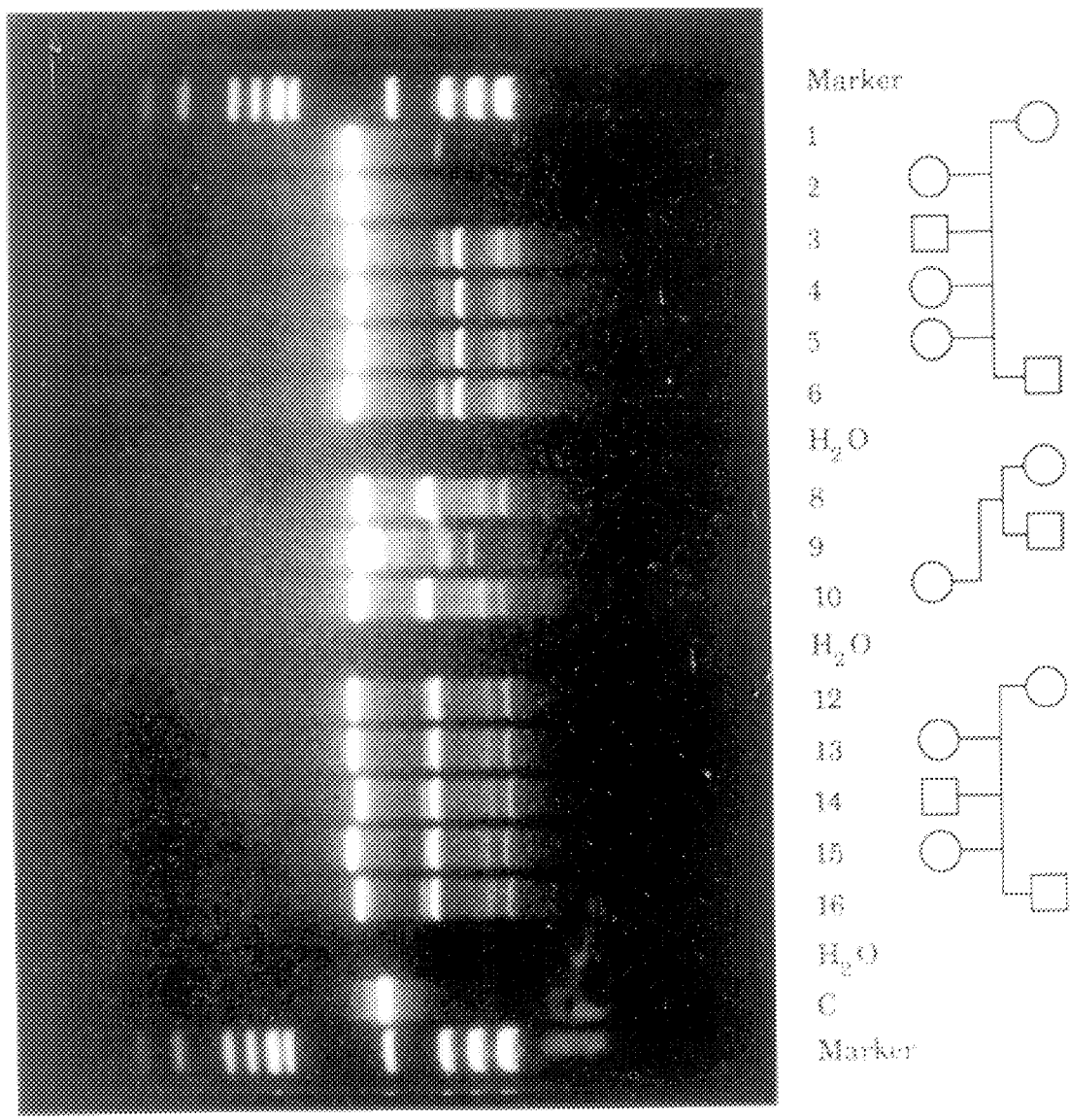
FIG. 5 Inheritance of 4F7 alleles was demonstrated by the analysis of DNAs from three pedigrees. DNA was prepared from a 20 ml sample of peripheral blood from each individual and analysis for alleles carried out using PCR amplification with the primers shown in FIG. 2A. The analysis shows the presence of two alleles in each individual and the Mendelian segregation of alleles through each pedigree. Amplification products were analyzed on a 1% agarose gel and size markers are HaeIII fragments of bacteriophage φx174.

Since the highly variable nature of the repeat element could conceivably result from rapid somatic mutation rather than segregation, the inheritance of this sequence element in DNA isolated from related individuals was investigated. DNA was obtained from individuals of three pedigrees and analyzed for alleles of the 4F7 repeat element by PCR amplification, demonstrating results consistent with Mendelian segregation. As is shown in FIG. 5, each individual displayed two distinct amplification products identical in size to one of a parent which, while not unambiguously demonstrating Mendelian segration, is inconsistent with frequent somatic mutation. Thus, it is reasonable to conclude that amplification products of this locus represent alleles of this repetitive element which are inherited in a Mendelian fashion.

Figure 6A:
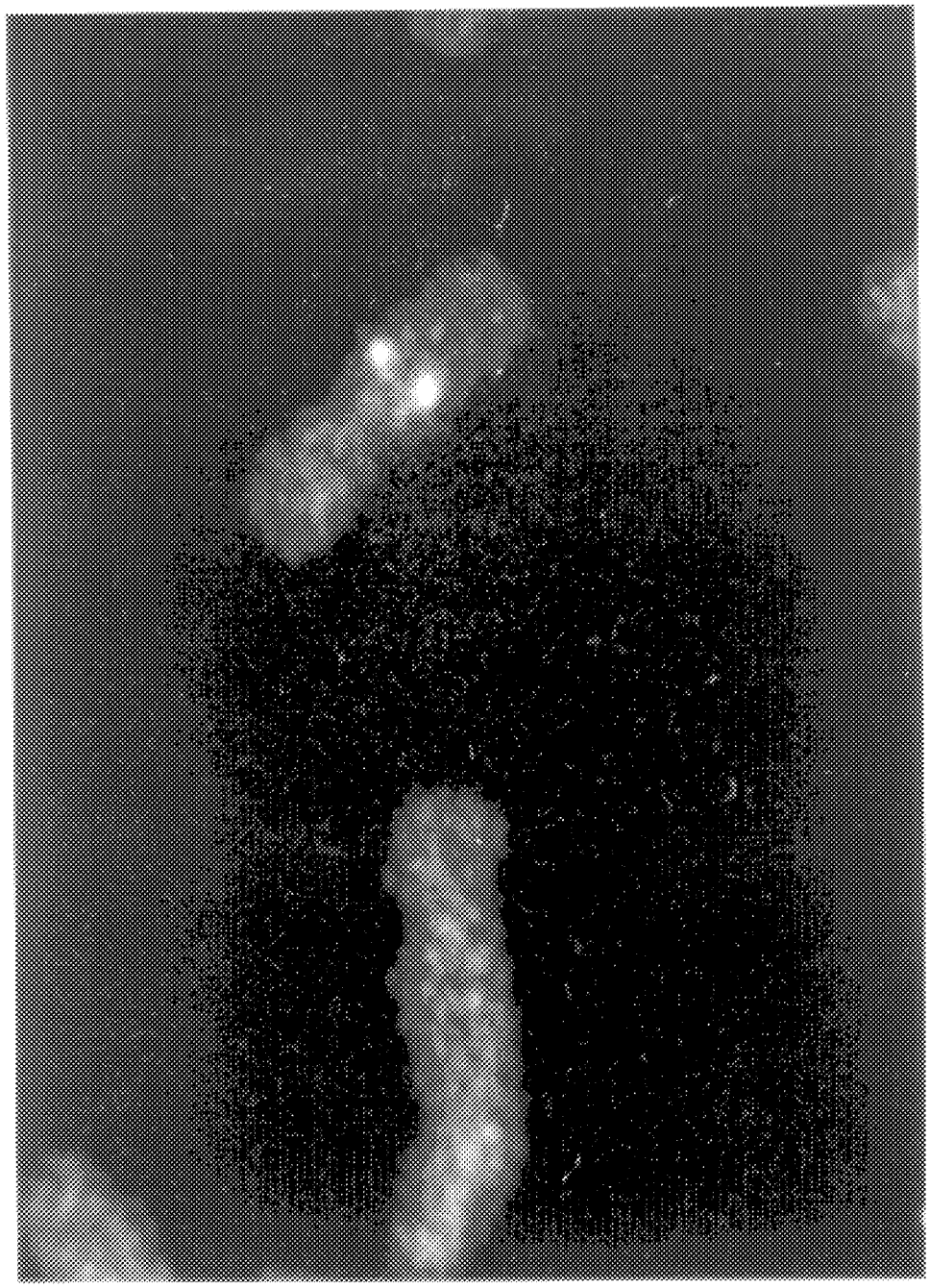
FIG. 6 Localization of cosmid 4F7 to chromosome 11 q13 by fluorescence in situ suppression hybridization. A. Cosmid DNA was labeled with biotinylated nucleotides using random hexamer priming, the repetitive sequences were blocked with human repetitive DNA, and fluorescence in situ suppression hybridization was carried out as previously described (Lichter, et al., *Science*, 247:64–69, 1990; Selleri, et al. *Proc. Natl. Acad. Sci. USA*, 88:887–891, 1990; and Selleri, et al. *Genetic Analysis Techniques and Applications*, 8:59–66, 1991). Chromosomes were prepared from a lymphoblast cell line with a normal human karyotype and the localization of the chromosome was determined using the method of Lichter, et al. (*Science*, 247:64–69,1990). B. Idiogram of human chromosome 11 showing the map location of polymorphic marker 4F7 relative to other previously mapped cosmid markers (Lichter, et al. *Science*, 247:64–69, 1990).
Figure 6B:
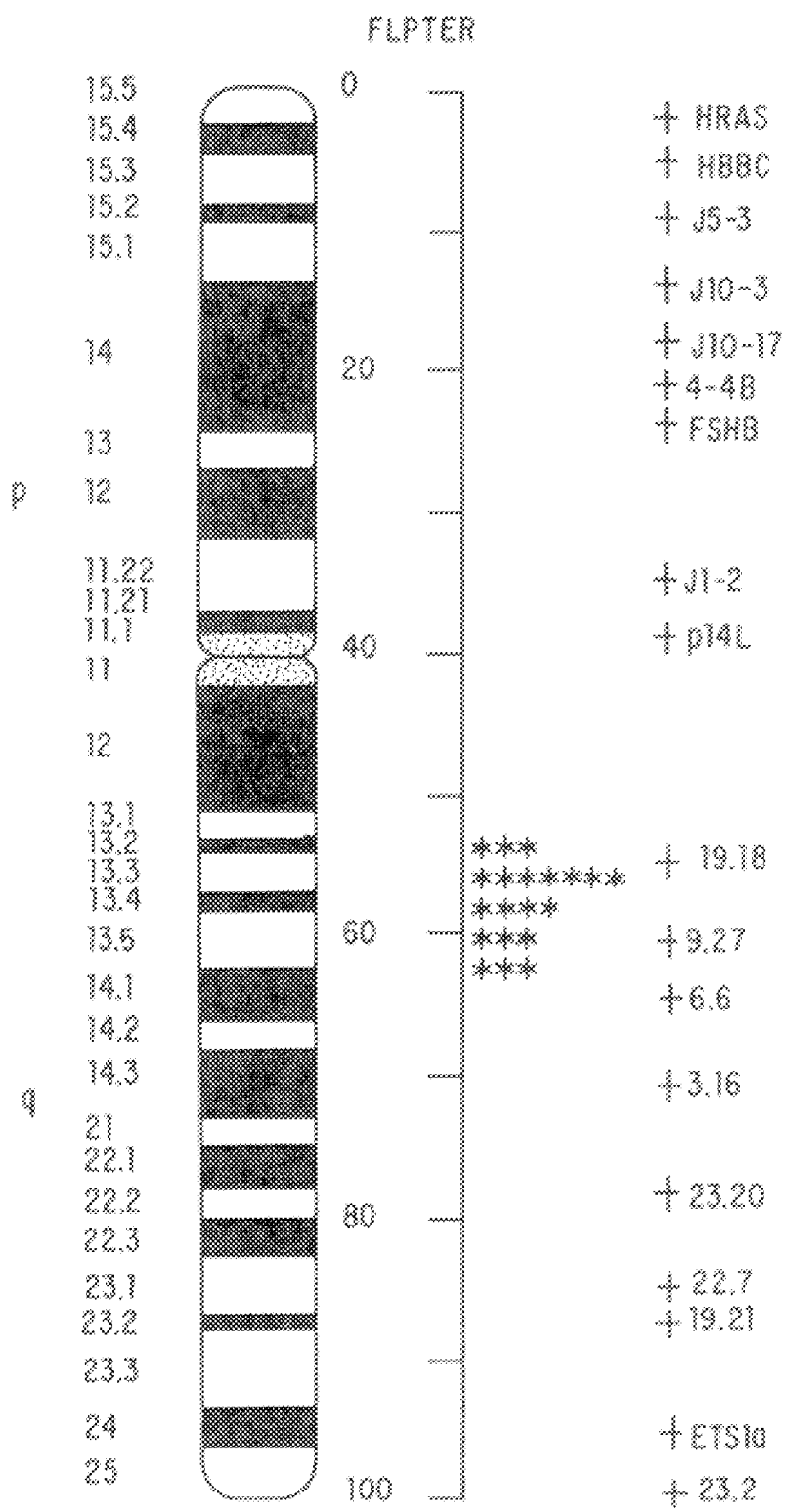

Further, since this marker could potentially be useful for genetic linkage studies, it would be valuable to determine the (1) precise chromosome localization, and (2) long range map of the locus. This cosmid was isolated from a chromosome-specific library where some of the members had been previously characterized by non-isotopic fluorescence in situ hybridization. Using methods of Lichter, et al. (Science, 247:64–69, 1990) and Selleri, et al. (Proc. Natl. Acad. Sci. USA, 88:887–891, 1990; Genetic Analysis Techniques and Applications, 8:59–66, 1991), DNA from cosmid 4F7 was labeled with biotinylated nucleotides by random hexamer primer, preannealed to remove repetitive DNA sequences, and hybridized to human metaphase chromosomes. The hybridization signal was visualized using FITC-avidin and FITC anti-avidin antibody, and images collected using confocal laser scanning microscopy (FIG. 6). Two distinct hybridization signals were seen on 95% of chromosomes 11 examined and no other cross-hybridizing signals were observed. Chromosomal position was determined using the method of Lichter, et al. (Science, 247:64–69, 1990) and the 4F7 clone was found to map at FLpter 0.6 (fractional chromosomal length from pter)±0.02. Comparison with the ideogram of chromosome 11 indicates a localization to 11 q13 with the most likely location 11q13.3–11q13.4. This probe was additionally localized within a panel of cosmid markers previously mapped to 11q13 by in situ hybridization (Lichter, et al., Science, 247:64–69, 1990).

The long range physical map surrounding this locus was established using pulsed field gel electrophoresis and the isolation and characterization of yeast artificial chromosomes (Brownstein, et al., Science, 244:1348–1351, 1989; Green and Olson, et al., Proc. Natl. Acad. Sci. USA, 87:1213–1217, 1990). DNA isolated from two human B lymphoblast cell lines was digested with several restriction endonucleases and pulsed-field gel electrophoresis carried out. TABLE 1 shows the fragment sizes for a series of CpG-rich restriction enzymes using the Apa1-Sac1 restriction fragment of the 4F7 cosmid. The location of the probe sequence within the cosmid is shown in FIG. 1.

TABLE 1

RARE RESTRICTION FRAGMENT SIZES

| Enzyme | WI-L2-729 | HHW1069 |
| --- | --- | --- |
| BssHII | 200 | 200 |
| Cla 1 | 280 | 280 |
| Eco 52 I | 240 | 180 |
| Mlu 1 | 580 | 580 |
| Not 1 | ND[a] | 440 |
| Sac II | 260 | 200 |
| Xho 1 | 200 | 200 |

[a]not determined

Figure 7:
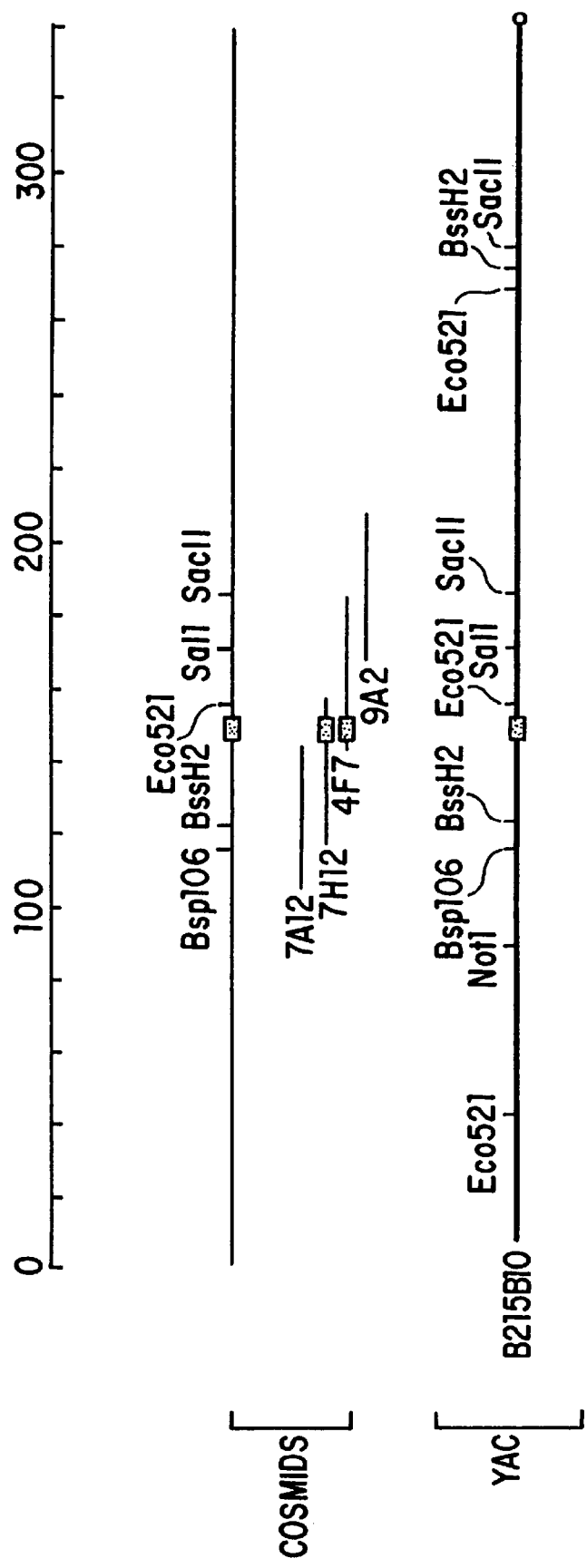
FIG. 7 Long range restriction map surrounding the 4F7 marker. The map was constructed using YAC and cosmid clone isolation based on probes from the 4F7 polymorphic locus. YAC clone B21 5B10 was obtained by PCR screening of a human genome YAC library (Green and Olson, *Proc. Natl. Acad. Sci. USA*, 87:1213–1217, 1990) and the location of restriction sites determined by partial digestion. Additional cosmid contigs, previously detected by multiplex analysis (Evans and Lewis, *Proc. Natl. Acad. Sci. USA*, 86:5030–5034, 1989) are also indicated on this physical map.

Yeast artificial chromosomes were isolated by screening a human YAC library with the polymerase chain reaction using primers detecting the 4F7 polymorphisms. YAC screening was carried out using a modification of the pool selection strategy (Green, et al., Proc. Natl. Acad. Sci. USA, 87:1213–1217, 1990) and YAC clones characterized on pulsed field gel electrophoresis. One YAC clone of 320 kb was isolated which contains the 4F7 repetitive element and the restriction map of this YAC clone was determined. Also, in a previous study in which cosmid contigs were constructed by hybridization multiplex analysis (Evans, et al., *Proc. Natl. Acad. Sci. USA,* 86:5030–5034, 1989), a contig was identified which included the 4F7 and 7H12 clones. The position of this contig in the physical map is indicated in FIG. 8. When combined with the pulsed field gel data, the resulting physical map spans a region of 400 kb in the vicinity of the repetitive element (FIG. 7) and demonstrates the location of at least two potential HTF islands, suggesting the locations of genes (Bird, *Trends Genet,* 3:342–347, 1987).

The invention now being fully described, it will be apparent to one of ordinary skill in the art that various changes and modifications can be made without departing from the spirit or scope of the invention.

SUMMARY OF SEQUENCES

SEQ ID NO: 1 is the nucleotide sequence of the core of a VNTR sequence which resembles the chi sequence of phage lambda.

SEQ ID NO: 2 is the nucleotide sequence of the core of a VNTR sequence such as found in the β-globin locus.

SEQ ID NO: 3 is the polymorphic hexanucleotide locus of the invention.

SEQ ID NO: 4 is the nucleotide sequence flanking the polymorphic locus at the 5' end.

SEQ ID NO: 5 is the nucleotide sequence flanking the polymorphic locus at the 3' end.

SEQ ID NO: 6 is an oligonucleotide sequence corresponding to a portion of the DNA sequence of the rat D2 dopamine receptor cDNA.

SEQ ID NO: 7 is an oligonucleotide primer which hybridizes to the nucleotide sequence flanking the polymorphic locus at the 5' end.

SEQ ID NO: 8 is an oligonucleotide primer which hybridizes to the nucleotide sequence flanking the polymorphic locus at the 3' end.

SEQ ID NO: 9 is the nucleotide sequence of a portion of a repetitive element in the genome of an individual.

We claim:

1. An oligonucleotide primer for identification of a human subject wherein the identification involves amplification of a genomic polymorphic locus, wherein the polymorphic locus consists of repetitive hexanucleotide sequences selected from the group consisting of:

(TGTATG), (TATATG), and (TATGTG)

wherein said primer is sufficiently complementary to non-repetitive sequences located at the 5' and 3' ends of said polymorphic locus to hybridize to the non-repetitive sequences.

2. Oligonucleotide(s) of claim 1, wherein the polymorphic locus includes the restriction site GTMKAC, wherein M is A or C and K is G or T.

3. Oligonucleotide(s) of claim 1 which hybridize with a flanking sequence selected from 5'-GCCTAGTCCCTGGGTGTGGTC-3' (SEQ ID NO: 4) or 5'-GGGGACATGTTCCCAGACCCCC-3' (SEQ ID NO: 5), and sequences, complementary thereto.

4. Oligonucleotide(s) of claim 3, which is 5'-GACCACACCCAGGGACTAGGC-3' (SEQ ID NO: 7) or 5'-GGGGGTCTGGGAACATGTCCCC-3' (SEQUENCE ID NO. 8), and sequences complementary thereto.

5. A method for identification of a human subject which comprises:

(a) amplifying a polymorphic locus present in the nucleic acid of the subject by means of primers which are sufficiently complementary to non-repetitive sequences located at the 5' and 3' ends of the polymorphic locus to hybridize to the non-repetitive sequences, wherein the polymorphic locus consists of hexanucleotide sequences selected from the group consisting of: (TGTATG), (TATATG), and (TATGTG); and (b) detecting the presence of the amplified polymorphic locus.

6. The method of claim 5, wherein the polymorphic locus is present on 11q13.

7. The method of claim 5, wherein the polymorphic locus includes the restriction site GTMKAC, wherein M is A or C and K is G or T.

8. The method of claim 5, wherein the oligonucleotide hybridizes with a non-repetitive sequence located at the 5' or 3' ends of the polymorphic locus and wherein the non-repetitive sequence is selected from 5'-GCCTAGTCCCTGGGTGTGGTC-3' (SEQUENCE ID NO. 4) or 5'-GGGGACATGTTCCCAGACCCCC-3' (SEQUENCE ID NO. 5), and sequences complementary thereto.

9. The method of claim 8, wherein the oligonucleotide is 5'-CGGATCAGGGACCCACACCAG-3' (SEQ ID NO:7) or 5'-CCCCTGTACAAGGGTCTGGGGG-3' (SEQ ID NO:8), and sequences complementary thereto.

10. The method of claim 5, wherein the amplified polymorphic locus is detected by gel electrophoresis.

11. The method of claim 5, which includes treating the amplified nucleic acid with an enzyme that recognizes the restriction site GTMKAC, wherein M is A or C and K is G or T.

12. A polynucleotide sequence which defines a genomic polymorphic locus, wherein the locus consists of repetitive hexanucleotide sequences selected from the group consisting of:

(TGTATG), (TATATG), and (TATGTG).

13. The isolated polynucleotide sequence of claim 12, wherein the polymorphic locus comprises the sequence AAABAX, wherein A is TATATG, B is TGTATG and X is selected from the group consisting of TGTATG and TATGTG.

14. An oligonucleotide primer for identification of a human subject wherein the identification involves amplification of a genomic polymorphic locus, wherein the polymorphic locus consists of at least two different hexanucleotide sequences selected from the group consisting of:

(TGTATG), (TATATG), and (TATGTG) wherein said primer is sufficiently complementary to non-repetitive sequences located at the 5' and 3' ends of said polymorphic locus to hybridize to said non-repetitive sequences.

15. The oligonucleotide primer of claim 1, wherein the polymorphic locus comprises the sequence AAABAX, wherein A is TATATG, B is TGTATG and X is selected from the group consisting of TGTATG and TATGTG.

16. The method of claim 5, wherein the polymorphic locus comprises the sequence AAABAX, wherein A is TATATG, B is TGTATG and X is selected from the group consisting of TGTATG and TATGTG.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..10

( x i ) SEQUENCE DESCRIPTION: SEQ ID NO:1:

G G G C A G G A R G         10

( 2 ) INFORMATION FOR SEQ ID NO:2:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..9

( x i ) SEQUENCE DESCRIPTION: SEQ ID NO:2:

G G G G T G G G G         9

( 2 ) INFORMATION FOR SEQ ID NO:3:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: CDS
    ( B ) LOCATION: 1..6

( x i ) SEQUENCE DESCRIPTION: SEQ ID NO:3:

T R T R T R          6

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..21

( x i ) SEQUENCE DESCRIPTION: SEQ ID NO:4:

G C C T A G T C C C    T G G G T G T G G T    C          2 1

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..22

( x i ) SEQUENCE DESCRIPTION: SEQ ID NO:5:

G G G G A C A T G T    T C C C A G A C C C    C C          2 2

( 2 ) INFORMATION FOR SEQ ID NO:6:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..60

( x i ) SEQUENCE DESCRIPTION: SEQ ID NO:6:

C C A C T C A C C C    A C C A C C T C C A    G G T A G A C A A C    C C A C G G C A T T    A C C A G T G T G G    C C A C C A G A A G          6 0

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS (B) LOCATION: 1..21

(x i) SEQUENCE DESCRIPTION: SEQ ID NO:7:

GACCACACCC AGGGACTAGG C                                                         21

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(i x) FEATURE:
        (A) NAME/KEY: CDS
        (B) LOCATION: 1..22

(x i) SEQUENCE DESCRIPTION: SEQ ID NO:8:

GGGGGTCTGG GAACATGTCC CC                                                        22

(2) INFORMATION FOR SEQ ID NO:9:

(i) SEQUENCE CHARACTERISTICS:
        (A) LENGTH: 870 base pairs
        (B) TYPE: nucleic acid
        (C) STRANDEDNESS: single
        (D) TOPOLOGY: linear (i i) MOLECULE TYPE: DNA (genomic)

(v i i) IMMEDIATE SOURCE:
        (B) CLONE: 4F7

(i x) FEATURE:
        (A) NAME/KEY: CDS
        (B) LOCATION: 1..870

(x i) SEQUENCE DESCRIPTION: SEQ ID NO:9:

```
ATATACAAGG CCTTTGCTGC TGCCCGGCCT GATGGAGAGG CCGGCTGCCA CCTTGAGCCA      60
GAGCAGGTAG GTGTGCTCGC TCGTGCAGAC CCCGAATGCC TTGAGTGGGG GTCCGGGGCA     120
GGGGTGCACG CGGTCAGGTA GGTATGCTCC GAGTGCAGAC CCCGAATGCC TTGAGTGGGG     180
GTCCGGGGCA GGGGTGCACA CACTCAGGTA GGTGTGCTGG TAGTGCAGAC CCCGAATACC     240
TTGAGTGGGG GTCCGGGGCA GGGTTGCACA TACTCAGGCC CATCTCCACC ATGGGCACAT     300
GGCCTCTTTT TGACAAAGTA TCTCTCTGCC TAGTCCCTGG GTGTGGTCAA TCATTTATCC     360
TTCTTCTTGT ATGTGTATGT GTGTATGTAT ATGTATATGT ATATGTATAT GTATATGTAT     420
ATGTATATGT ATATGTATAC GTGTACGTGT ACGTGTACGT GTACGTGTAC GTGTATGTGT     480
GTGTGTATGT GTATGTGTAT GTGTATGTGT ATGTATATGT GTATGTGTAT GTATATGTAT     540
ATGTGTATGT ATATGTATAT GTATGTGTAT ATGTATATGT GTATGTGTAT GTATATGTAT     600
ATGTATGTGT ATGTGTATAT GTGTATGTAT ATGTATATGT ATATGTATGT GTATATGTAT     660
ATGTATATGT GTATGTATAT GTATATGTAT GTGTATATGT ATATGTATAT GTGTATGTAT     720
ATGTATATGT ATGTGTATAT GTATATGTAT ATGTGTATGT ATATGTATAT GTGTATGTAT     780
ATGTGTATGT GTATGTATAT GTGTATGTAT CGGGTACCGT AGTCCCCCTT ATCCACTGGG     840
GACATGTTCC CAGACCCCCA GCGGATGCTG                                      870
```